United States Patent
Wang et al.

(10) Patent No.: US 6,483,892 B1
(45) Date of Patent: Nov. 19, 2002

(54) VOLUMETRIC COMPUTED TOMOGRAPHY (CT) FLUOROSCOPY SYSTEM FOR SMALL ANIMAL STUDIES

(76) Inventors: Ying Wang, 3812 Chamberlyne Way, Norman, OK (US) 73072; Ying Liu, 1405 Aburdeen Ct., Iowa City, IA (US) 52246

( * ) Notice: Subject to any disclaimer, the term of this patent is extended or adjusted under 35 U.S.C. 154(b) by 0 days.

(21) Appl. No.: 10/035,696

(22) Filed: Oct. 20, 2001

(51) Int. Cl.[7] .................................................. G21H 7/00
(52) U.S. Cl. .................................. 378/43; 378/62; 378/9
(58) Field of Search ............................ 378/4, 9, 43, 62

(56) References Cited

U.S. PATENT DOCUMENTS 6,271,534 B1 * 8/2001 Kumakhov .............. 250/505.1

* cited by examiner

Primary Examiner—David V. Bruce (57) ABSTRACT

This invention describes a dynamic X-ray imaging system for small animal studies and other applications that include a volumetric CT fluoroscopy (VCTF) scanner and software, which operates in accordance with a generalized Feldkamp algorithm or any other suitable reconstruction methods. The VCTF system is a significant advancement of current micro-CT techniques. While prior micro-CT systems are featured by relatively slow data acquisition and static image reconstructions, the present invention includes real-time data acquisition hardware, a dedicated real-time image reconstruction algorithm, an extra-fast cone-beam reconstruction engine, and integrating them into a 4D micro-CT scanner. The system of the present invention can be constructed relatively economically using state-of-the-art x-ray source, electronic detector techniques and image reconstruction methods.

7 Claims, 7 Drawing Sheets

Five-star-shaped data acquisition system (DAS), which consists of five source-detector assemblies.

Figure 1. Block diagram of the data processing, transmission and storage system for the proposed volumetric CT fluoroscopy scanner.

Figure 2. Equiangular fan-beam geometry, in which diverging rays from the source are detected by a linear detector array with each detector extending the same angular increment.

Figure 3. Redundant regions in a fan-beam half-scan.

Figure 4. Five-star-shaped data acquisition system (DAS), which consists of five source-detector assemblies.

Figure 5. Minimum angular range for reconstruction using the five-star DAS equals $\pi/5+10\Delta$.

Figure 6. Numerical simulation demonstrating superior temporal resolution using the five-star DAS.
(a) True section at z=-0.25 of the 3D Shepp-Logan phantom, (b) Feldkamp reconstruction of (a),
(c) five-star half-scan reconstruction corresponding to (b),
(d) Feldkamp reconstruction of the phantom with a moving component (indicated by the arrow), and
(e) five-star half-scan reconstruction corresponding to (d).

Figure 7. Flowchart of the five-star half-scan Feldkamp-type reconstruction.

VOLUMETRIC COMPUTED TOMOGRAPHY (CT) FLUOROSCOPY SYSTEM FOR SMALL ANIMAL STUDIES

ACKNOWLEDGEMENT

This invention was made with government support a SBIR grant from the National Institutes of Health (R43RR15325-01).

BACKGROUND OF THE INVENTION

Although small animal models have been found indispensable in medical research, their potential has not been fully explored yet, because of a current limitation that the animals have to be sacrificed for analysis. This prevents researchers from observing in vivo the natural or perturbed physiological/pathological processes in a noninvasive and repeatable fashion. Tomographic imaging is the only approach for providing multi-dimensional data about biochemical, genetic or pharmacological processes in vivo. Therefore, NCI initiated the Small Animal Imaging Resource Programs.

Neoplasms have an intrinsic spatially distributed nature. Typically, tumors develop in different sites, metastasize to other sites and are internally heterogeneous. To reveal the characteristics of tumors, spatially distributed and temporally varied measurements need to be taken, preferably with contrast enhancement. Imaging is a key resource for studying the development, growth and therapeutic response of neoplasms, especially in the oncologic settings. It is well known that administration of a contrast material provides a short temporal window for optimally imaging the vasculature, lesions and tumors. Contrast enhancement imaging becomes increasingly important for functional studies of lesions and tumors. Analysis of volumetric and dynamic images of small animals will lead the way to application of quantitative methods in human beings.

Over the past several years, tremendous progress has been made in X-ray detector techniques, real-time/volumetric CT algorithms, and computing resources. Development of a volumetric CT fluoroscopy (VCTF) system for small animal studies has just become commercially feasible. It would be desirable to make volumetric CT fluoroscopy a vital tool in biomedical laboratories for various applications, especially small animal studies, such as contrast-enhancement dynamic imaging for diagnosis and treatment of tumors.

Currently, small animal imaging systems are rarely available, which severely restricts studies of tumors in model systems. Most biomedical imaging devices have been tuned for human studies and have suboptimal performance for small animal studies and their tumors. Therefore, it is desirable to scale down imaging systems for significantly improved images of mouse-sized objects. Micro-CT systems have been proved useful for studying bony structures, solid organs and soft tissues. With contrast enhancement, micro-CT allows 3D-motion analysis and functional imaging. Because of its unique imaging capabilities and relatively low cost, micro-CT has been established as a unique imaging modality for small animal studies in cancer research.

In 1987, Flannery et al. applied the 2D CCD array technology in micro-CT. In the 1990s, a number of micro-CT systems were constructed. Most of these systems employ CCD cameras, micro-focus x-ray tubes, and have image resolutions between 20–100 $\mu$m. A major application of micro-CT scanners is small animal imaging. In recent prototypes of such systems, the data acquisition system rotates about an animal table, while in earlier systems an animal stage is rotated in a fixed data acquisition system These imaging systems permit screening of small animals for mutations or pathologies and monitoring of disease progression and response to therapy. A state-of-the-art micro-CT scanner for small animal imaging was developed by Paulus et al. at the Oak Ridge National Laboratory. Their scanner was demonstrated to be effective for detection and characterization of soft-tissue structures, skeletal abnormalities, and tumors in live animals. The scanner allows rapid data acquisition (5–30 minutes) and provides high-resolution images (<50 $\mu$m).

A system known as the Dynamic Spatial Reconstructor (DSR) was developed at Mayo Clinic [Ritman et al., 1985]. In the DSR, 28 X-ray tubes are arranged in a semicircle in a circular gantry. Projections formed on the fluorescent screen arc, scanned via multiple imaging chains, and reconstructed volumetrically. Nevertheless, the DSR suffers from a number of drawings, including its complexity and high cost.

A cone-beam X-ray microtomographic imaging systems has been developed [Pan et al., 1998]. This microtomographic imaging system consists of a conventional dental X-ray source (Astech 65), a sample translation and rotation stage, and X-ray scintillation phosphor screen, and a high resolution slow scan cooled CCD camera (Kodak KAF 1400). An epoxy embedded human inner ear specimen was studied using this system [Pan et al., 1998]. The source-to-detector distance and the specimen-to-detector distance were 70 mm and 11 mm, respectively. One hundred equal angular projections were captured by the CCD camera with a 12 bit dynamic range and 1317×967 detectors covering 30×22 mm$^2$ on the phosphor screen. Each projection was integrated over 0.16 second, and normalized against the background. Volumetric images have been successfully reconstructed [Wang et al., 1993; Pan et al., 1998].

SUMMARY OF THE INVENTION

The present invention relates to a system for use in small animal studies and other applications that include a volumetric CT fluoroscopy (VCTF) scanner and operates in accordance with a novel method that draws from the Feldkamp algorithm The VCTF system is a significant advancement of micro-CT techniques known in the prior art, and has important and immediate applications for small animal studies. While prior micro-CT systems are featured by relatively slow data acquisition and static image reconstructions, the present invention includes real-time data acquisition hardware, a dedicated real-time image reconstruction algorithm, and an extra-fast cone-beam reconstruction engine, and integrating them into a 4D micro-CT scanner.

The system of the present invention can be constructed relatively economically using state-of-the-art source and CCD techniques. Novel image reconstruction methods improve upon prior systems, such as the DSR.

DETAILED DESCRIPTION OF THE INVENTION

With an X-ray point source and a 2D-detector array, X-rays intersecting a spherical object form a cone, giving rise to the nomenclature "cone-beam tomography". The cone-beam approach is desirable for faster data collection, higher image resolution, better radiation utilization and easier hardware implementation, therefore it attracts more and more attention in material, biological, medical and other studies.

Despite progress in exact cone-beam reconstruction, approximate cone-beam algorithms remain important. The advantages of approximate cone-beam reconstruction include the following. First, incomplete scanning loci can be used. The completeness condition for exact reconstruction requires that there exist at least a source position on any plane intersecting an object to be reconstructed. In many cases of X-ray CT, this condition cannot be satisfied. Second, partial detection coverage is permissible. In exact cone-beam reconstruction, the cone-beam is assumed to cover an object entirely from any source position. However, complete detection coverage is generally impossible in medial X-ray CT. Third, computational efficiency is high. Because of the partial detection, approximate reconstruction involves much less raw data. The computational structure of Feldkamp-type approximate cone-beam reconstruction is fairly straightforward, highly parallel, hardware-supported, and particularly fast for reconstruction of a small region of interest (ROI). Fourth, image noise and ringing artifacts can be less. With the 3D Fourier method, we found that exact cone-beam reconstruction produced more ringing as compared to the Feldkamp method. This type of ringing is believed to be inherent to all exact cone-beam reconstruction formulas that take the second derivative data.

The system uses a novel, generalized Feldkamp algorithm. The Feldkamp algorithm [Feldkamp et al., 1984], which has been the most popular approximate cone-beam algorithm. In the present system, the Feldkamp cone-beam algorithm is generalized to allow simultaneous handling of continuous data streams from multiple X-ray sources for improved temporal resolution. The generalized Feldkamp cone-beam algorithm can be adapted into special cases, including helical/helix-like cone-beam scanning.

The X-ray CT fluoroscopy (CTF) is to perform X-ray tomographic imaging in real-time to enable image guidance of interventions, synchronization of scanning with contrast bolus arrival, and motion analysis, particularly functional imaging, as well as other applications. However, filtered backprojection, the current method for CTF image reconstruction, is subject to increased image noise associated with reduced tube current, as well as motion and metal artifacts from implants, needles or other surgical instruments. The system also uses a known row-action/ordered-subset EM algorithm for CTF. Because time-dependent variation in images is localized during CTF, the row-action EM CTF algorithm converges rapidly. Also, this iterative CTF algorithm effectively suppresses image noise in both numerical simulation and real data experiments [Wang et al., 1999].

Fiber coupled CCD systems, lens coupled CCD systems, and COMS detector systems and other types of detection systems suitable for use in the 4D micro-CT scanner are preferably x-ray quantum noise limited and provide high spatial resolution, wide dynamic range, and high contrast sensitivity. A stereo-image guidance system can be included. Such a system can include, for example, two 1k×1k frame-transfer CCDs, each acquiring 30 frames per second. The electronic system regulates the data flow of the multiple detectors and integrates real-time frame grabbing, image processing and display.

The volumetric CT fluoroscopy (VCTF) system produces sufficient temporal, spatial and contrast resolution for small animal studies. The elements of the system include the VCTF scanner device and a Feldkamp-type software package with optimized system/algorithm parameters.

The data acquisition system consists of five pairs of an x-ray tube and a 2D CCD camera or another type of 2D detection system, which is also referred to as a five-star data acquisition system. The number of x-ray sources can also be other integers, such as 3, 7, 8, and so on. Additional filtration can be added if it is needed for a scan of a specific subject. The rotation required for cone-beam CT is provided by a motorized stage. The source-to-axis distance is fixed at 90 cm in the initial prototype, and the detector-to-axis distance is adjustable from 10–60 cm through precision translation stages. This unique mechanism allows a tradeoff between the spatial resolution and the field of view in specific studies. The positions of these components are aligned under an optical collimator, as known in the art. By combination of this configuration and a Feldkamp-type reconstruction software package, the micro-CT fluoroscopy system is believed capable of a temporal resolution of about 0.1 second and a spatial resolution down to 0.14 mm.

In the Feldkamp-type reconstruction framework, the cone-beam reconstruction is essentially handled as a fan-beam reconstruction problem In fan-beam geometry, two sets of complete projections are collected during a full-scan (360°). It is known that one complete set of projections is obtained over a half-scan (180° plus two fan-angles). Hence, using our five-star data acquisition system, approximately a one-tenth of a full scan (about 40°) is needed to collect a complete set of projections for reconstruction of a volume in cone-beam geometry. It is also known in the art that the number of projections in a complete data set should be determined as a function of detector parameters. To reconstruct a volume of $256^3$ voxels, there should be about 200 projections in a complete data set. Therefore, each of the five CCD cameras should capture 40 frames (200/5) per one-fifth scan. Let the data acquisition system rotate 360° every 2 seconds that is mechanically feasible with conventional techniques, a data-rate of 200 frames per second is required of the CCD camera. With these settings, a complete data set can be gathered in about 0.2 seconds, which is 2–3 times faster than prior CT fluoroscopy systems. A reconstructed image can be updated within a fraction of a half-scan in the context of CT fluoroscopy because time-dependent image variation is spatially localized. Therefore, we estimate that the temporal resolution of the proposed system would be about 0.1 second or less.

The data acquisition module is based on advanced but well-known frame-transfer CCD technology or other suitable data acquisition techniques. The preferred CCD detector array acquires digital data at a rate of 60 frames per second, 1024×1024 pixels per frame, or an even better performance. Using frame transfer CCD, the exposure duty cycle of the imaging system is increased by nearly 100 times as compared to conventional CCD technology. In a 4×4 binning mode (256×256), the detector array acquired 240 frames per second. The module includes a CsI (T1) scintillator (Hamamatsu, Bridgewater, N.J.), a 2.5:1 optical fiber taper (Income Fiber Optics, Mass.), and a frame transfer CCD (MedOptics, Ariz.). The pixel size of the CCD is 0.024 mm, therefore in a 4×4 binning mode, the spatial resolution of the detector module (on the surface of the scintillator) is about 0.24 mm (Given an optical magnification of 2.5 times, the resolution is 0.024×4×2.5=0.24 mm). As mentioned above, the detector-to-axis distance can be specified by a user between 10 and 60 cm, (or other preferred distance range), relative to a source-to-axis distance of 90 cm (or another preferred distance). High precision stepping motors and closed-loop control devices are utilized to move detectors and sources to adjust detector-to-axis distances, and source-to-axis distances. Slipping ring technologies and closed-loop control devices are also utilized to control the rotation of the assembly of the detectors and the sources. This unique mechanism allows a tradeoff between the spatial resolution and the field of view in specific studies. For instance, with a detector-to-axis distance of 60 cm, the spatial resolution is maximized to 0.14 mm, while the field of view is 3.7 cm in diameter. With a detector-to-axis distance of 10 cm, the field of view is maximized to 5.5 cm in diameter, while the spatial resolution is degraded to about 0.22 mm.

Each detector is equipped with a thermal-electric cooler. The overall additive noise (read noise and thermal noise) at the above frame rate is less than 100 electrons. The total quantum gain of the cascaded CsI-fiber-CCD chain is about 19 electrons for each x-ray photon absorbed by the scintillator. Based on the measurement of a current fiber coupled CCD prototype using an identical CsI (T1) scintillator, the detective quantum efficiency (DQE) of the detector module is estimated to be 70.

Figure 1:
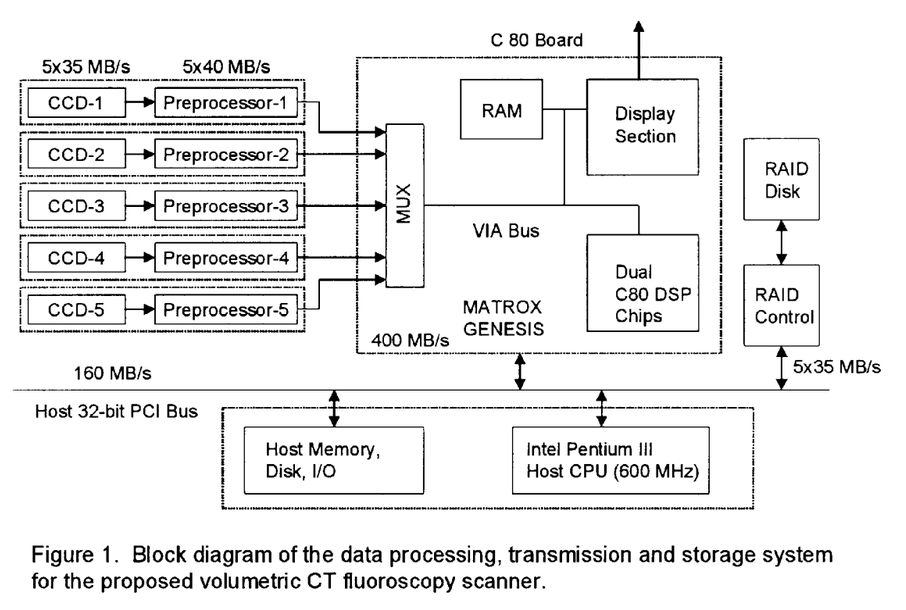
FIG. 1 is a block diagram illustrating the electronics of the exemplary system

FIG. 1 is a block diagram of the data acquisition, preprocessing, transmission and storage system The system includes five CCD cameras. Each CCD camera acquires 240 frames (256×256×12 bits) per second, hence the entire system operates at 1200 frames per second, generating data at a rate of 150 MB per second. In the intended applications, the imaging duration is typically 3 to 5 seconds and repeated as many as 5 times for certain procedures, defining a storage requirement of roughly 3–5 GB per animal. The digital data from each CCD camera are read into a preprocessing chip (Far West Sensor Corp., Garden Grove, Calif.), which performs real-time pixel-wise calculations. The CCD-to-CCD uniformity and geometrical and other corrections will be made "on the fly" using this chip. A multiplexer (MUX) selects the preprocessed frames, and routes the data to the on-board memory of a C80 board (Model: Genesis; Matrox Electronic Systems Ltd., Doval, Quebec, Canada) at a sustained rate of 400 MB per second. The board manages two concurrent data streams: one to a real-time display and the other to a host memory from where the data stream is written to the redundant array independent disks (RAID; Storage Concept, Irvine, Calif.). A cluster of five RAID devices will be utilized corresponding to each of the five CCD cameras. Each of the selected RAID devices is capable of storing 32 GB data with a sustained bandwidth of 35 MB per second. The throughput of the selected RAID systems exceeds the input data throughput, as required. The image grabbing, multiplexing and display is handled by the Matron Image Library (MIL) software utilities. The PCI board (Matrix Genesis) integrates real-time frame grabbing, preprocessing and display based on the commercially available TMS320C80 technology or other suitable technology.

Filtered backprojection is a well-known image reconstruction method for CTF/CT. As used herein, the term "Feldkamp-type reconstruction" is intended to refer to a ID filtered backprojection mechanism for image reconstruction in cone-beam geometry. The generalized Feldkamp algorithm [Wang et al., 1993], several other practical cone-beam algorithms [Gullberg and Zeng, 1992, Yan and Leahy, 1992], as well as spiral CT algorithms [Crawford and King, 1990, Taguchi and Aradate, 1998] can be regarded as special cases of the Feldkamp-type reconstruction. In the illustrated embodiment of the invention, the Feldkamp-type reconstruction approach is used for real-time volumetric X-ray imaging.

In conventional Feldkamp-type cone-beam reconstruction, a transaxial slice is reconstructed using projection data collected form a 360° angular range (full-scan). In conventional fan-beam reconstruction, there are two complete sets of projection data over a full-scan range. These two sets are redundant, because exact reconstruction can be achieved just using projection data of 180° plus two fan-angles (half-scan). Although projection data are insufficient for accurate and reliable construction of off-midplane structures using traditional Feldkamp-type algorithms, it can be intuitively appreciated that there are "approximate redundancy" in the data acquired along geometric rays that would be identical in the absence of any fan-beam tilting angle and any longitudinal translation between the X-ray tube and the object being scanned. In other words, the "redundant" data are acquired along the X-ray paths having the same horizontally projected line but in opposite directions.

There are many possible weight functions for half-scan fan-beam image reconstruction, such as Parker's weight function and Gullberg and Zeng's weight function. The illustrated embodiment of the invention utilizes our generalized Parker weight function.

Figure 2:
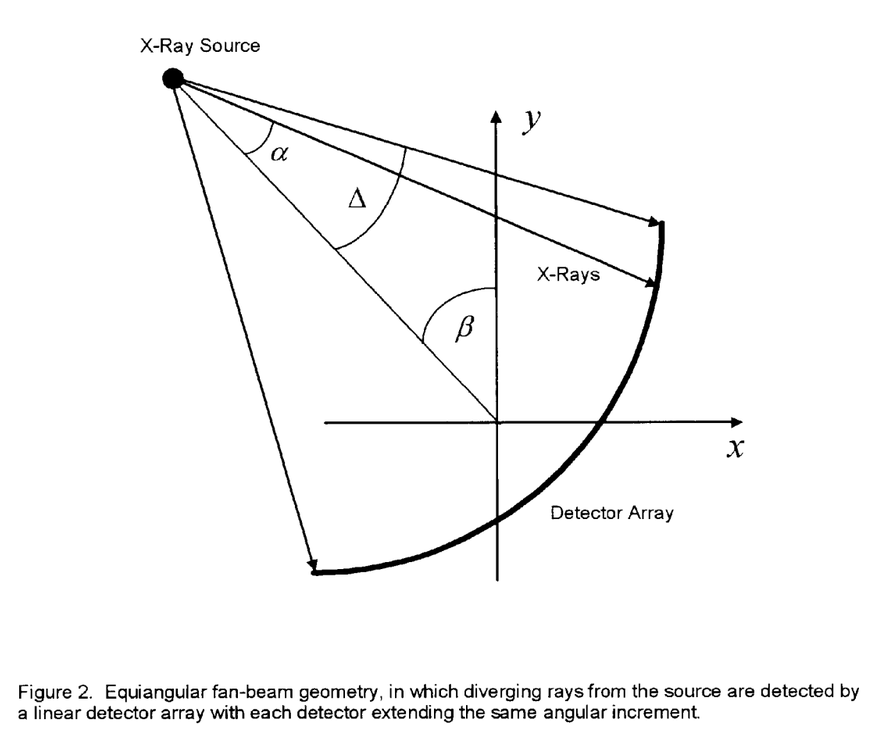
FIGS. 2–5 illustrate the geometry of the system.
Figure 3:
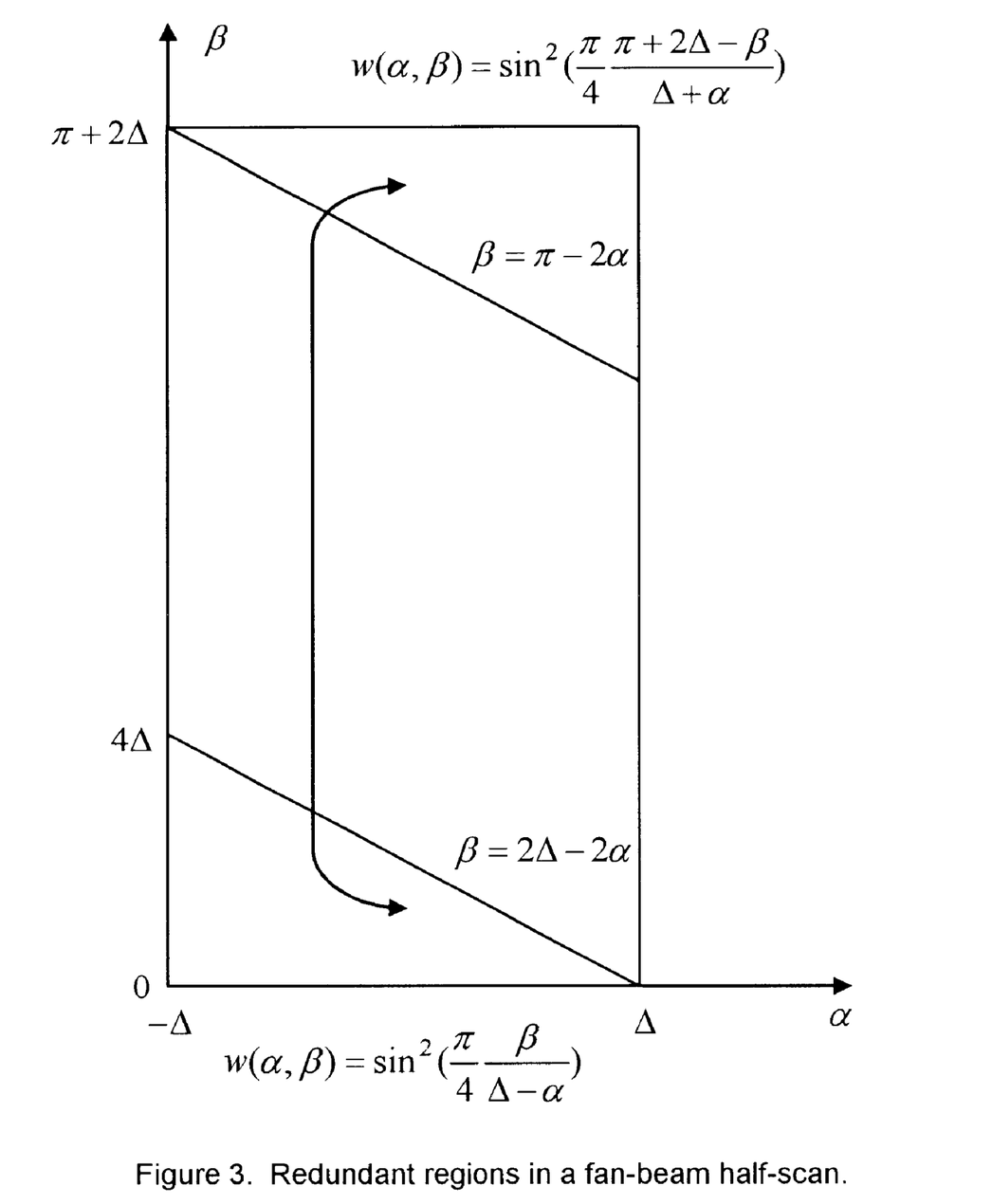

As shown in FIG. 2, the equiangular fan-beam geometry is assumed, where, $\beta$ denotes the angular position of an X-ray source, $\gamma$ the angular position of a detector, and $\Delta$ the fan-beam angle. FIG. 3 summarizes Parker's classic design of the single-source half-scan weighting function. In FIG. 3, the upper and lower triangles are sampled twice; hence the data in the two regions must be combined for doubly sampled Radon locations to make a unit contribution in image reconstruction. Specifically, the weighting scheme Parker proposed is described as follows:

$$w(\alpha, \beta) = \begin{cases} \sin^2\left(\frac{\pi}{4}\frac{\beta}{\Delta-\alpha}\right), & 0 \le \beta \le 2\Delta - 2\alpha; \\ \sin^2\left(\frac{\pi}{4}\frac{\pi+2\Delta-\beta}{\Delta+\alpha}\right), & \pi - 2\alpha \le \beta \le \pi + 2\Delta; \\ 1, & 2\Delta - 2\alpha \le \beta \le \pi - 2\alpha. \end{cases}$$

Figure 4:
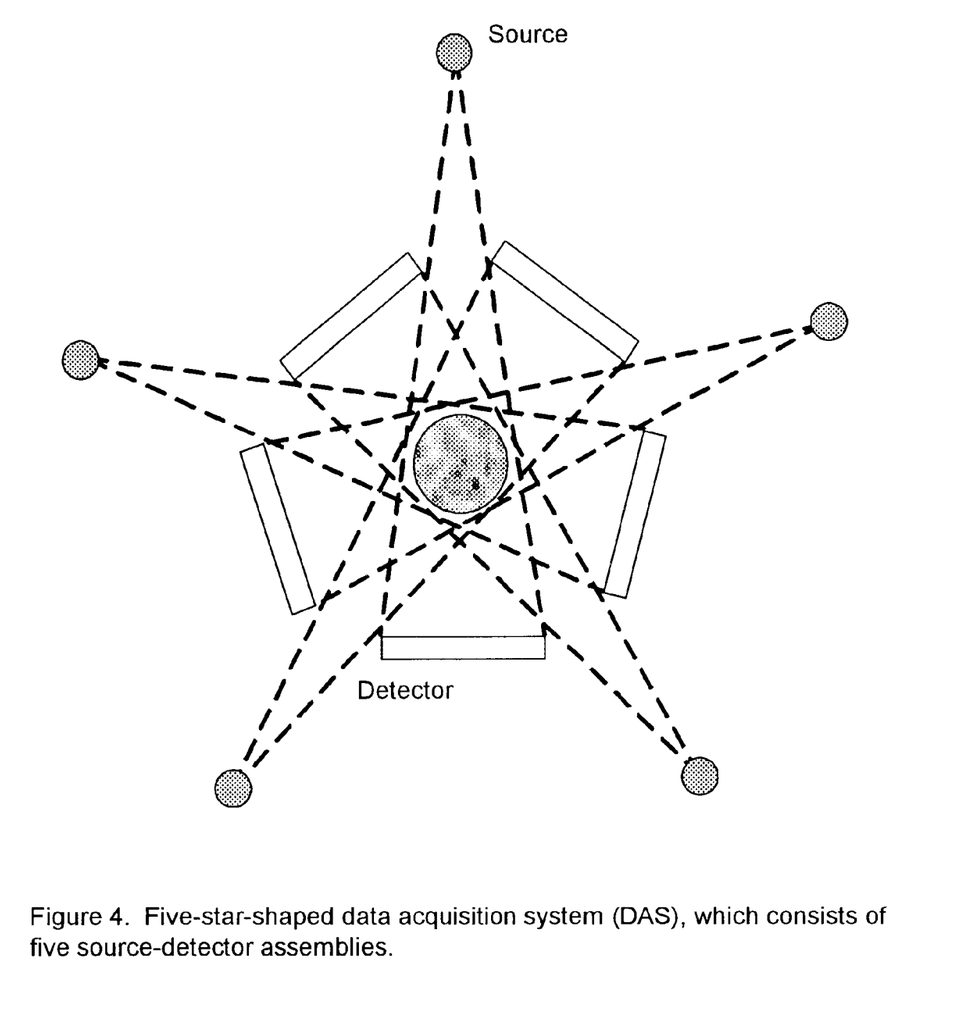
Figure 5:
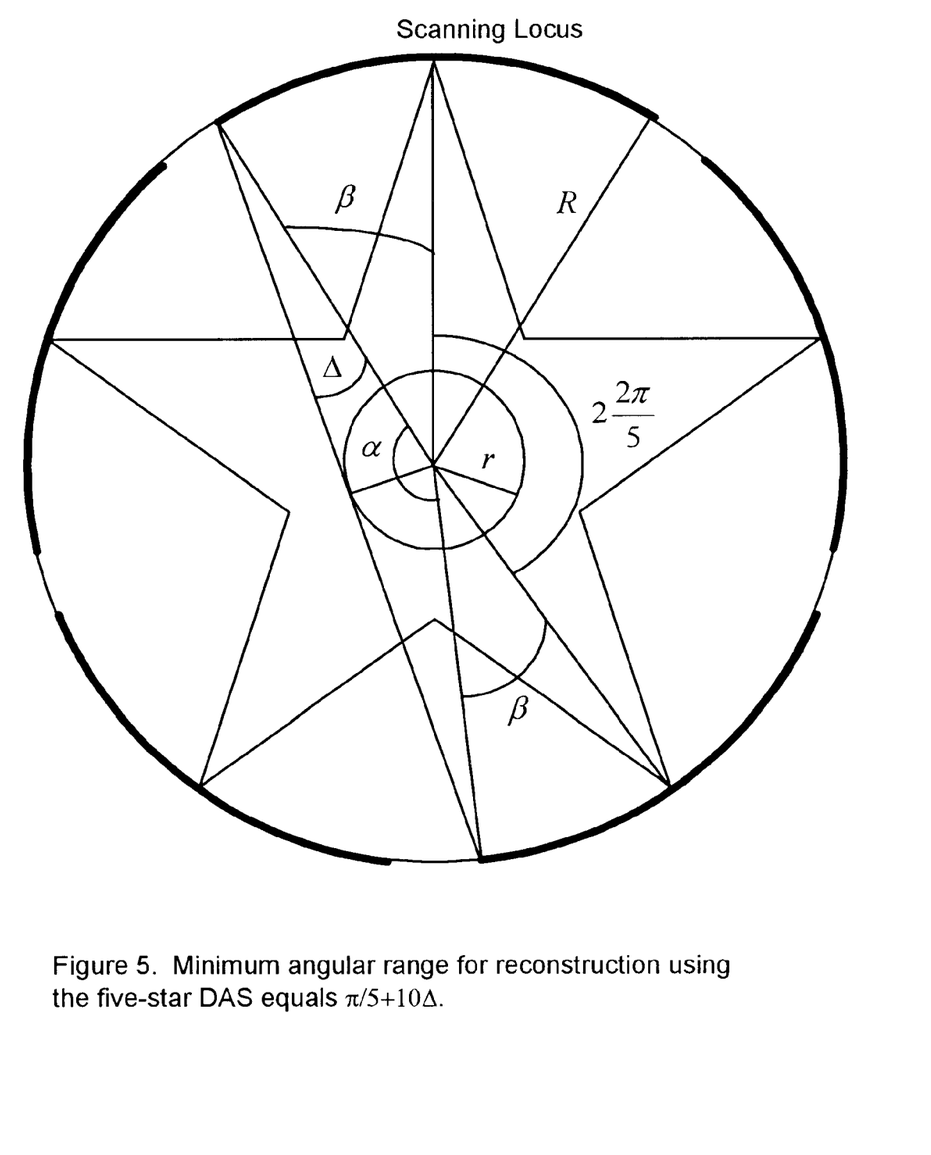

We have generalized Parker's weighting scheme into the case of N x-ray sources and cone-beam geometry [Liu et al., 2001]. In the case of N x-ray sources that are symmetrically distributed with respect to the reconstruction system origin, for the optimal temporal resolution the minimum source angular range should be used to collect a set of complete projection data. As shown in FIGS. 4 and 5 for the case of N=5, the minimum source angular range is $\pi/N+2\Delta$. We have generalized Parker's weighting scheme into the case of N x-ray sources:

$$w(\alpha, \beta; i) = \begin{cases} \sin^2\left(\frac{\pi}{4} \frac{\beta - 2i\pi/N}{\Delta - \alpha}\right), & 2i\pi/N \le \beta \le 2i\pi/N + 2\Delta - 2\alpha; \\ \sin^2\left(\frac{\pi}{4} \frac{(2i+1)\pi/N + 2\Delta - \beta}{\Delta + \alpha}\right), & (2i+1)\pi/N - 2\alpha \le \beta \le (2i+1)\pi/N + 2\Delta; \\ 0, & (2i+1)\pi/N + 2\Delta \le \beta \le (2i+2)\pi/N; \\ 1, & \text{otherwise,} \end{cases}$$

where i=0, ..., N−1. It can be verified that after the N-source half-scan weighting the weight is a unit at each Radon location, and continuous at the boundaries of the redundant regions.

The following five-star half-scan generalized Feldkamp-type cone-beam reconstruction formula is then obtained:

$$g(x, y, z; t) = \frac{1}{2} \sum_{i=0}^{4} \int_{\omega(t-t_0)+2i\pi/5}^{\omega(t-t_0)+(2i+1)\pi/5} \frac{R^2}{(R-v)^2} \int_{-\infty}^{\infty} w(\alpha, \beta; i) D(\beta, p, \zeta; i) f\left(\frac{Ru}{R-v} - p\right) \frac{R}{\sqrt{R^2 + p^2 + \varsigma^2}} dp \, d\beta,$$

where $g(x,y,z;t)$ represents a time-varying image volume, R the source-to-origin distance, $\beta$ the angular source position, D(.) cone-beam projection data, $u = x \cos \beta + y \sin \beta$, $v = -x \sin \beta + y \cos \beta$, $\zeta = Rz/(R-v)$, f(.) is the ramp filter, $\omega$ is the speed of the X-ray source rotation, time $t > t_0 = (\pi/N + 2\gamma_m)/\omega$, $\gamma_m$ the fan-angle in the mid-plane.

Clearly, the reconstructed image $g(x,y,z;t)$ is assumed to be a function of time, and so is the projection data. If an object to be reconstructed is motionless, there would be no discontinuities among N=5 subsets/segments of consecutive projections. However, inconsistency among adjacent projections, especially among N=5 segments of projections, can be taken into account and effectively suppressed to further suppress motion artifacts. Therefore, it would be useful to: (1) make use of a complete set of projection data from a minimum time span, and (2) approximately combine overlapping projection data from different segments so that any major jumps are filtered out.

Alternative reconstruction methods can be employed. After projection data are acquired in real-time over an extended period, there are two options for image reconstruction: on-line and off-line. The on-line reconstruction is important for interventional procedures that demand immediate feedback for optimal results. The off-line reconstruction is relatively less critical in terms of computational time. In either mode of image reconstruction, a fast speed is desirable. Reasonably fast off-line image reconstruction is presently contemplated. The alternative real-time image reconstruction strategy is to utilize special hardware and/or optimized methods, especially dedicated 3D backprojectors. Special cards that may be suitable are commercially available from TeraRecon Inc. (San Mateo, Calif., USA; http://www.terarecon.com) which take 15 seconds to reconstruct an image volume of 2563 voxels from 288 projections.

Figure 6:
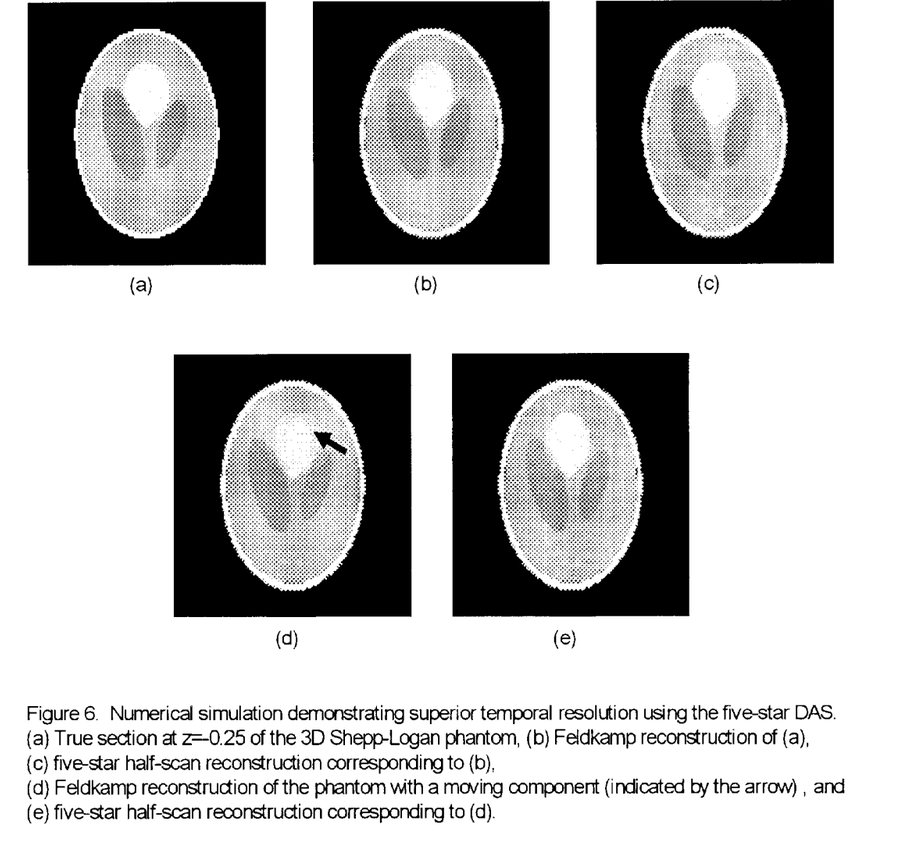
FIG. 6 illustrates the results of numerical simulation of the system
Figure 7:
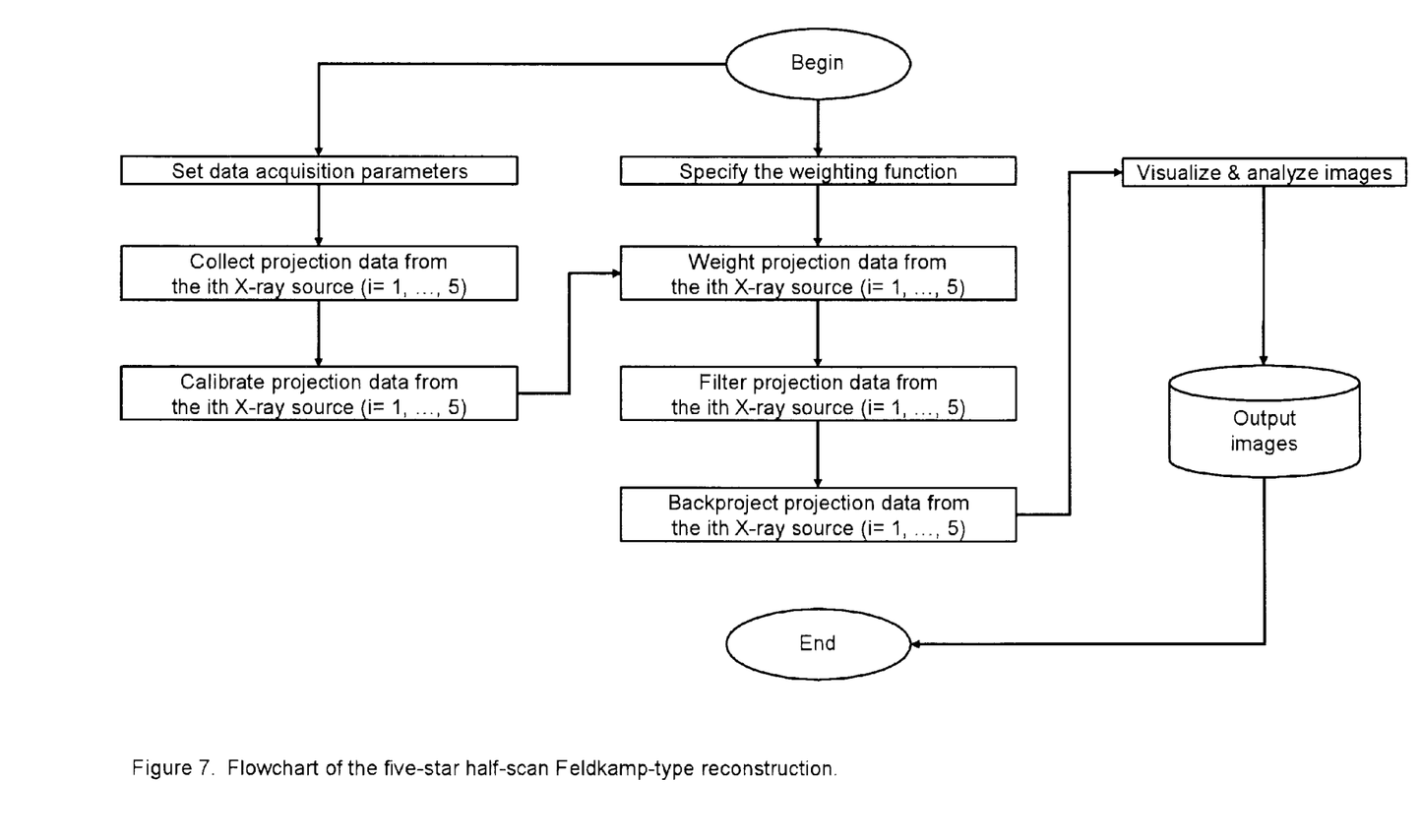
FIG. 7 is a flow diagram illustrating the method of operation of the system.

Numerical simulations have been conducted to test the real-time volumetric CT algorithm. Using synthesized idealized objects with known contrast dynamics and geometric features, error components were numerically generated with respect to data acquisition and image reconstruction parameters. FIG. 6 shows numerical simulation that demonstrates superior temporal resolution using the five-star data acquisition system and the five-star Feldkamp-type reconstruction algorithm outlined in FIG. 7.

What claimed is:

1. An X-ray micro-CT system with multiple sources for dynamic and volumetric imaging of small animals.

2. The system of claim 1, wherein filtered backprojection type reconstruction programs are used that make use of a generalized half-scan weighting scheme, such as what we described above or modified in the same spirit.

3. The system of claim 2, wherein dedicated hardware/workstation may be used for accelerated data preprocessing, image reconstruction and/or image visualization.

4. The system of claim 3, wherein any interventional procedure may be performed that is guided by the images observed or derived.

5. The system of claim 4, wherein advanced data acquisition components and/or systems are integrated for desirable imaging performance.

6. The system of claim 5, wherein Internet computing/communication techniques may be applied to enhance the overall utilities of the system.

7. The system of claim 6, wherein other relevant physiologic device and measures may be used in any synergic fashion.

* * * * *